(12) United States Patent
Sauer et al.

(10) Patent No.: US 7,112,700 B1
(45) Date of Patent: Sep. 26, 2006

(54) EFFICIENT AND ECONOMIC ASYMMETRIC SYNTHESIS OF NOOTKATONE, TETRAHYDRONOOTKATONE, THEIR PRECURSORS AND DERIVATIVES

(75) Inventors: Anne M. Sauer, Baton Rouge, LA (US); William E. Crowe, Baton Rouge, LA (US); Roger A. Laine, Baton Rouge, LA (US); Gregg Henderson, St. Gabriel, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/106,338

(22) Filed: Apr. 14, 2005

(51) Int. Cl.
*C07C 45/00* (2006.01)
*C07C 35/00* (2006.01)

(52) U.S. Cl. .................. 568/348; 568/374; 568/819; 568/820

(58) Field of Classification Search .............. 568/820, 568/591, 348, 374, 819; 549/341
See application file for complete search history.

(56) References Cited

U.S. PATENT DOCUMENTS 3,819,711 A * 6/1974 Bozzato .................. 568/350

OTHER PUBLICATIONS

Marshall, J. et al., "The Total Synthesis of Racemic Isonootkatone (α-Vetivone)," *Chem. Commun.*, pp. 753-754 (1967).
Revial, G. et al., "Enantioselective synthesis of (+)-α-vetivone through the Michael reaction of chiral amines," *Tetrahedron: Asymmetry*, vol. 11, pp. 4975-4983 (2000).
Torii, S. et al., "Functionalization of trans-decalin. V. A synthesis of (±)-nootkatone and (±)-valencene from 4β,4aβ-dimethyl-$\Delta^{6,7}$-octalin-1-one ethylene acetal," *Bull. Chem. Soc. Jpn.*, vol. 55, pp. 887-890 (1982).
van der Gen, A. et al., "Stereoselective synthesis of eremophilane sesquiterpenoids from β-pinene," *Recueil Trav. Chim. Pays-Bas*, vol. 90, pp. 1034-1044 (1971).
Yanami, T. et al., "Synthetic Study of (+)-Nootkatone from (−)-β-Pinene," *J. Organic Chem.*, vol. 45, pp. 607-612 (1980).

* cited by examiner

*Primary Examiner*—Sikarl A. Witherspoon
(74) *Attorney, Agent, or Firm*—John H. Runnels

(57) ABSTRACT

An inexpensive, stereoselective synthesis for nootkatone, tetrahydronootkatone, and their derivatives is disclosed. The starting materials used in the synthesis are inexpensive. The principal starting material, (−)-β-Pinene, is on the GRAS list (generally recognized as safe).

13 Claims, 3 Drawing Sheets

EFFICIENT AND ECONOMIC ASYMMETRIC SYNTHESIS OF NOOTKATONE, TETRAHYDRONOOTKATONE, THEIR PRECURSORS AND DERIVATIVES

The development of this invention was funded in part by the Government under grant number 58-6435-8-084 awarded by the Department of Agriculture, Agricultural Research Service. The Government has certain rights in this invention.

This invention pertains to the synthesis of nootkatone and its derivatives.

Nootkatone, whose IUPAC nomenclature is 4,4a,5,6,7,8-hexahydro-6-isopropenyl-4,4a-dimethyl-2(3H)-naphtha-lone, and whose structure is depicted as Compound 9 in FIG. 1, occurs naturally in certain plant sources including cedar, vetiver grass, and citrus oils. Nootkatone has a fragrance reminiscent of grapefruit, and is used commercially as a flavor or fragrance ingredient. Nootkatone is nontoxic to humans and other mammals.

Nootkatone has activity, however, as a repellant or toxicant against various arthropods, including termites, ants, flies, ticks, mole crickets, and cockroaches; as well as against certain other invertebrates including nematodes. Nootkatone also acts as an environmentally-friendly wood preservative. See, e.g., published international patent application WO 01/28343; and published United States patent application US-2003-0073748-A1.

Nootkatone is expensive, however, which impedes its broader use for these and other purposes. There is an unfilled need for an efficient and economical synthesis of nootkatone, tetrahydronootkatone, and other nootkatone derivatives; preferably a synthesis that is stereoselective, so that the products have the desired biological activity; and preferably a synthesis that is based on starting materials that are on the GRAS (generally recognized as safe) list, to reduce the burdens of regulatory approval. No prior synthesis of nootkatone has satisfied all of these criteria. Most of the nootkatone sold commercially to date has been produced by the semi-synthetic oxidation of the orange oil component valencene. Valencene is an expensive starting material.

J. Marshall et al., "The Total Synthesis of Racemic Isonootkatone (α-Vetivone)," *Chem. Commun.*, pp. 753–754 (1967) suggested that the compound α-vetivone should be considered an isomer of nootkatone, and that it should be renamed isonootkatone. A multi-step synthesis of racemic α-vetivone (or isonootkatone) from diethyl isopropylidene malonate was described.

A. van der Gen et al., "Stereoselective synthesis of eremophilane sesquiterpenoids from β-pinene," *Recueil Trav. Chim. Pays-Bas*, vol. 90, pp. 1034–1044 (1971) disclosed a multistep synthesis of 2-methyl-4-isopropylidenecyclohexanone from β-pinene. Robinson annulation of 2-methyl-4-isopropylidenecyclohexanone with trans-3-penten-2-one stereoselectively produced α-vetivone, which could then be converted to nootkatone.

S. Torii et al., "Functionalization of trans-decalin. V. A synthesis of (±)-nootkatone and (±)-valencene from 4β,4aβ-dimethyl-$\Delta^{6,7}$-octalin-1-one ethylene acetal," *Bull. Chem. Soc. Jpn.*, vol. 55, pp. 887–890 (1982) disclosed a multi-step synthesis of racemic nootkatone and racemic valencene from 4β,4aβ-dimethyl-$\Delta^{6,7}$-octalin-1-one ethylene acetal.

G. Revial et al., "Enantioselective synthesis of (+)-α-vetivone through the Michael reaction of chiral amines," *Tetrahedron: Asymmetry*, vol. 11, pp. 4975–4983 (2000) disclosed a multi-step synthesis of (+)-α-vetivone, involving the stereoselective Michael addition of a chiral imine of 4-isopropylidene-2-methylcyclohexanone to phenyl crotonate.

T. Yanami et al., "Synthetic Study of (+)-Nootkatone from (−)-β-Pinene," *J. Organic Chem.*, vol. 45, pp. 607–612 (1980) disclosed a multi-step synthesis of (+)-nootkatone from (+)-nopinone, the latter of which could be prepared by the oxidation of β-Pinene. The authors described their key step as the conjugate addition of methallyltrimethylsilane to trans-3-ethylidenenopinone, which was obtained from nopinone by cross-condensation with acetaldehyde followed by acid treatment. The dione that was obtained from the resulting adduct was methylated, followed by ozonization, to produce nootkatone hydrochloride upon treatment with hydrogen chloride. Regioselective dehydrochlorination of the hydrochloride produced nootkatone. An alternative route using allyltrimethylsilane was also described.

Prior methods for synthesizing nootkatone have one or more of the following disadvantages: the synthesis is lengthy; the synthesis requires relatively expensive starting materials; the yield is low; the synthesis produces a racemic mixture; or one or more starting materials are not on GRAS list (generally recognized as safe).

There is an unfilled need for a less expensive method for the stereoselective synthesis of nootkatone. While the current high price of nootkatone may be tolerable in certain fields of use, such as flavorings and fragrances, it would still be desirable to have a less expensive source of nootkatone even for such purposes. However, the high cost of nootkatone precludes commercial use in other areas, for example as a repellant or toxicant against termites or other pests. If nootkatone could be produced far more inexpensively than is currently the case, it would become commercially feasible to use it and its derivatives as a repellant or toxicant against various arthropods, including termites, ants, flies, ticks, mole crickets, and cockroaches; as well as against certain other invertebrates such as nematodes. It could also become commercially feasible to use it as a wood preservative for protection against wood-destroying insects.

We have discovered a novel, inexpensive, stereoselective synthesis for nootkatone, tetrahydronootkatone, and their derivatives. The starting materials used in the synthesis are inexpensive. The principal starting material, (−)-β-Pinene, is a natural compound on the GRAS list (generally recognized as safe). The synthesis is shorter, less expensive, and of significantly higher yield than prior synthetic schemes for nootkatone.

Our experimental data have shown that the synthetic scheme outlined in FIG. 1 stereoselectively yields nootkatone as the exclusive product. The starting material was converted to this single product.

EXAMPLE 1

Figure 1:
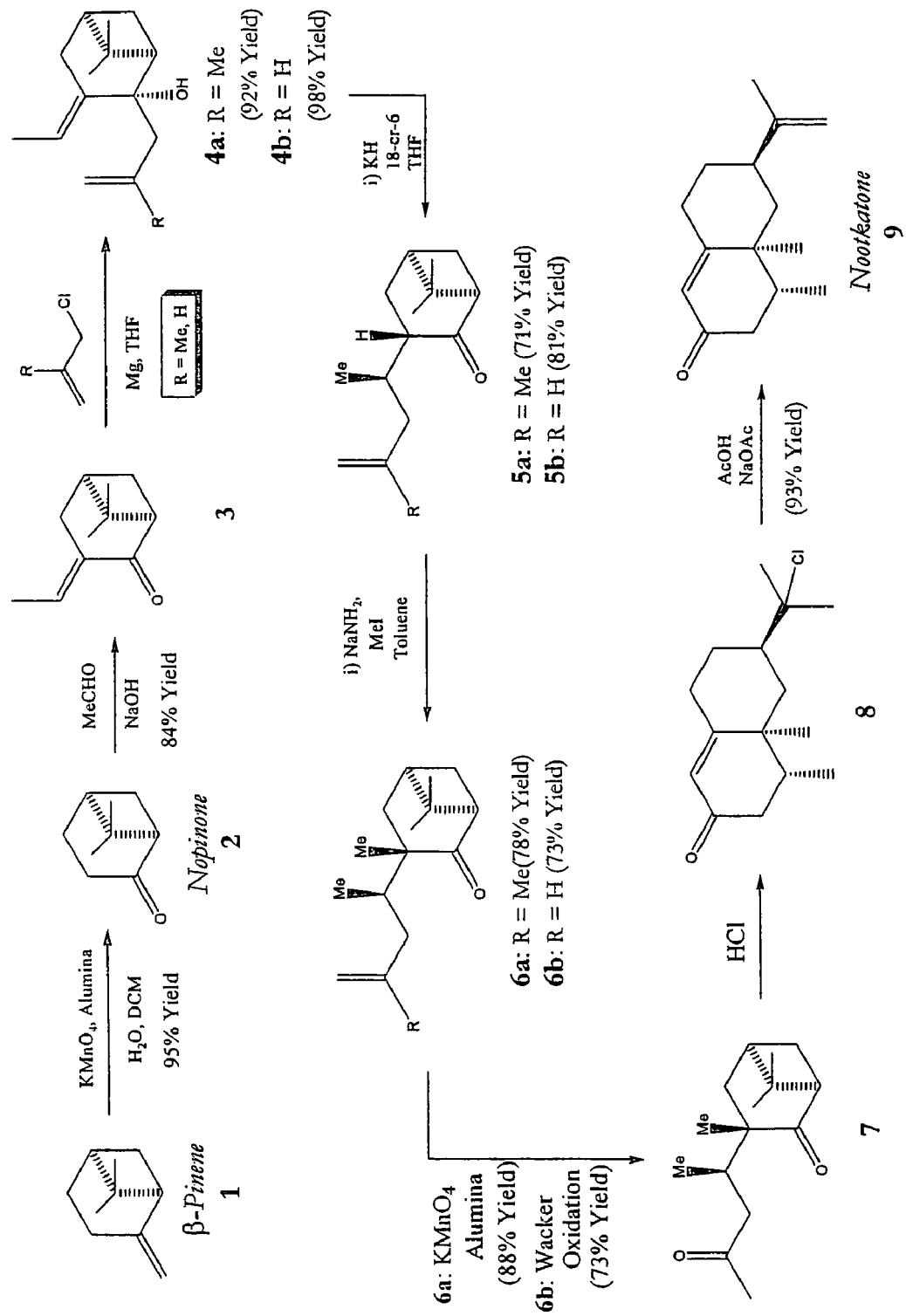
FIG. 1 depicts an embodiment of a synthetic scheme in accordance with the present invention.

6,6-dimethyl-bicyclo [3.3.1]heptan-2-one, Nopinone (Compound 2): Finely ground $KMnO_4$ (2.8 g, 17.8 mmol), acidic alumina (Brockmann Activity 1, 11.2 g, 0.1098 mol), and water (2.79 g, 0.1552 mol) were mixed for five minutes to produce a homogeneous mixture. Commercially-obtained (−)-β-Pinene (0.5 g, 0.582 mL, 3.67 mmol) was dissolved in dichloromethane (DCM) (100 mL), and the solution was placed in a round bottom flask. The moistened permanganate/alumina mixture was added in small portions to this solution over a 10 minute period with continual stirring. The reaction was allowed to proceed at room temperature, and the progress of the reaction was monitored by TLC (90:10/hexane: EtOAc). After essentially all starting material had reacted, the crude mixture was filtered through a fritted glass funnel, and the residue was washed with DCM (2×50 mL). Excess solvent was removed via rotary evaporator to leave a yellow oil, which was further purified by column chromatography (90:10/hexane: EtOAc) to give colorless Compound 2 (0.48 g, 95% yield). $^1$H NMR: (250 MHz, CDCl$_3$), δ 2.7–2.5 (m, 3H), 2.42–2.29 (m, 1H), 2.27–2.2 (m, 1H), 2.13–1.87 (m, 2H), 1.61–1.57 (d, J=9.46, 1H), 1.33 (s, 3H), 0.86 (s, 3H). $^{13}$C NMR: (62.5 MHz, CDCl$_3$), δ 214.77, 57.94, 41.10, 40.30, 32.57, 25.88, 25.17, 22.10, 21.31.

EXAMPLE 2

(1R,5R)-6,6-dimethyl-3-E)-ethylidenebicyclo[3.3.1]heptan-2-one (Compound 3): A magnetic stir bar was placed in a clean, dry, 3-neck, jacketed, round bottom flask fitted with a constant addition funnel and two inlet valves. The flask was then purged with argon. Compound 2 (1 g, 1.0194 mL, 7.24 mmol) and KOH (0.4872 g, 8.7 mmol) were dissolved in ethanol (17.2 mL) in the flask, under argon. The resulting solution was cooled to 5° C. A solution of acetaldehyde (0.609 mL, 0.4781 g, 10.9 mmol) in EtOH (4.3 mL) was added to the flask over 30 minutes, still under Ar. The mixture was allowed to react at 5° C. for 15 hours. At 15 hour intervals, four additional portions of acetaldehyde (0.609 mL) in EtOH (4.3 mL) were added to the reaction mixture, which was held at 5° C. After the final portion of acetaldehyde and EtOH was added, stirring was continued an additional 6 hours. Then p-toluenesulfonic acid monohydrate (1.927 g, 10.1 mmol) in EtOH (5 mL) was added to the mixture, and the resulting solution was stirred for 3 hours at room temperature. The solvent was removed via rotary evaporator, and the remaining crude brown residue was then dissolved in ether. The ether solution was passed through a series of dry columns (with a 90:10/Hexane: EtOAc solvent), and the eluted solution was then distilled in a Kugelrohr apparatus (85–95° C., 3 mmHg) to give Compound 3 (1 g, 84% yield) as a colorless liquid. $^1$H NMR: (250 MHz, CDCl$_3$), δ 6.89–6.86 (m, 1H), 2.59–2.56 (m, 4H), 2.21 (m, 1H), 1.81–1.77 (m, 3H), 1.46 (m, 1H), 1.35 (s, 3H), 0.86 (s, 3H). $^{13}$C NMR: (62.5 MHz, CDCl$_3$), δ 202.48, 134.76, 134.00, 55.5, 40.5, 38.98, 27.9, 27.8, 26.2, 21.6, 13.7.

As an alternative, NaOH may be used as the base in this synthesis, in lieu of KOH.

EXAMPLE 3

3-ethylidene-6,6-dimethyl-2-(2-methyl-allyl)-bicyclo[3.1.1]heptan-2-ol (Compound 4a): A solution of methallylchloride (0.692 g, 7.64 mmol) in freshly distilled tetrahydrofuran (THF) (2.5 mL) was added to a suspension of flame-dried Mg metal turnings (0.28 g, 11.5 mmol) in THF (2.5 mL) over 30 minutes at 60° C. The resulting Grignard solution darkened during heating at reflux for an additional 20 minutes. The mixture was then cooled to −42° C. (dry ice/chlorobenzene bath), and a solution of the enone Compound 3 (0.4182 g, 2.6 mmol) in THF (2.5 mL) was added dropwise. After 5 minutes, the cooling bath was removed, and the reaction was stirred for 1.5 hours as it warmed to room temperature. The mixture was then decanted into ice-cold 0.1 N HCl (50 mL) and extracted with ether. The combined organic fractions were washed with water and brine, dried over Na$_2$SO$_4$, filtered, and concentrated. Column chromatography (with 90:10/Hexane: EtOAc) provided Compound 4a (0.52 g, 92% yield) as a colorless liquid. $^1$H NMR: (250 MHz, CDCl$_3$), δ 0.973 (s 3H), 1.05–1.01 (d 1H), 1.21 (s 3H), 1.60–1.57 (d of t, 3H), 1.61 (s 3H), 1.92 (s 3H), 2.63–2.18 (m 5H), 4.82–4.65 (m 2H), 5.79–5.77 (m 1H); $^{13}$C NMR (62.5 MHz, CDCl$_3$) δ 13.1, 22.4, 24.7, 27.3, 30.1, 31.6, 37.9, 38.7, 48.9, 49.8, 78.7, 114.4, 122.0, 143.2, 143.4.

EXAMPLE 4

2-allyl-3-ethylidene-6,6-dimethyl-bicyclo[3.1.1]heptan-2-ol (Compound 4b): Mg metal turnings (0.33 g, 13.7 mmol) were placed in a clean, dry round bottom flask and flame-dried under vacuum. Freshly-distilled THF (2.5 mL) was added to the flask, and the contents were heated to reflux. The mixture was cooled to 40° C., and a solution of allyl chloride (0.75 mL, 0.70 g, 9.1 mmol) in THF (2.5 mL) was added dropwise over a 30 minute period. The resulting Grignard solution was held at 40° C. for an additional 20 minutes. The mixture was then cooled to −42° C. (dry ice/chlorobenzene bath), and a solution of the enone Compound 3 (0.5 g, 3 mmol) in THF (2.5 mL) was added dropwise. After 5 minutes, the cooling bath was removed, and the reaction was stirred for 1.5 hours as it warmed to room temperature. The mixture was then decanted into ice-cold 0.1 N HCl (50 mL) and extracted with ether. The combined organic fractions were washed with water and brine, dried over Na$_2$SO$_4$, filtered, and concentrated. Column chromatography (with 90:10/Hexane: EtOAc) provided Compound 4b (0.62 g, 98% yield) as a colorless liquid.

$^1$H NMR: (250 MHz, CDCl$_3$), δ 0.976 (s 3H), 1.03 (s 1H), 1.19 (s 3H), 1.58–1.61 (d of t, 3H), 1.82 (s 1H), 1.92 (s 1H), 1.95 (s 1H), 2.27–2.67 (m 5H), 4.97–5.07 (m 2H), 5.79–5.83 (m 2H); $^{13}$C NMR (62.5 MHz, CDCl$_3$) δ 13.1, 22.4, 27.2, 29.3, 31.5, 38.1, 38.8, 46.7, 49.1, 78.3, 117.7, 122,1, 134.8, 142.9.

EXAMPLES 5 AND 6

General Procedure for Oxy-Cope Rearrangement (Conversion of Compound 4a to Compound 5a, or of Compound 4b to Compound 5b): Under an argon atmosphere, oil-free potassium hydride, KH (4.1 mmol) was placed in a round bottom flask. Freshly distilled THF (35 mL) was cannulated into the flask, and the contents were stirred at 0° C. Alcohol 4a or 4b (2.4 mmol) was added to the flask, followed immediately by a solution of 18-crown-6 in THF (2.4 mmol) via cannulation. The mixture was allowed to react at 0° C. for ~6 hours. The reaction was then quenched with a phosphate buffer solution (pH=7), and the contents were extracted with ether. The combined organic layers were washed with water and brine, and dried over Na$_2$SO$_4$. After filtration, excess solvent was removed under vacuum to provide crude product 5a or 5b, respectively.

3-(1,3-dimethyl-but-3-enyl)-6,6-dimethyl-bicyclo[3.1.1]heptan-2-one (Compound 5a): Purified Compound 5a (0.49 g, 71%) was obtained by column chromatography (with a 90:10/Hexane: EtOAc solvent). $^1$H NMR: (250 MHz, CDCl$_3$), δ 0.79 (s 3H), 0.93–0.90 (d 3H), 1.32 (s 3H), 1.73–1.68 (s and q overlapping, 5H), 2.12–1.95 (m 3H), 2.42–2.25 (m 1H), 2.47–2.43 (m 1H), 2.57–2.50 (m 2H), 2.65–2.60 (m, —OH, 1H), 4.76 4.71 (d 2H); $^{13}$C NMR (62.5 MHz, CDCl$_3$) δ 15.3, 21.2, 21.8, 25.8, 26.8, 27.6, 40.6, 43.2, 43.5, 44.9, 57.9, 111.9, 144.0, 215.9.

6,6-dimethyl-3-(1-methyl-but-3-enyl)-bicyclo[3.1.1]heptan-2-one (Compound 5b): Purified Compound 5b (0.4 g, 81%) was obtained by column chromatography (90:10/Hexane: EtOAc). $^1$H NMR: (250 MHz, CDCl$_3$), δ 0.70 (s 3H), 0.87–0.84 (d 3H), 1.22 (s 3H), 1.65–1.61 (d 2H), 2.09–1.96 (m 3H), 2.38–2.19 (m 3H), 2.49–2.44 (t 1H), 2.73–2.61 (m, —OH, 1H), 4.99–4.90 (m 2H), 5.71–5.60 (m 1H); $^{13}$C NMR (62.5 MHz, CDCl$_3$) δ 15.4, 21.3, 22.3, 25.7, 26.7, 30.2, 39.2, 40.5, 43.4, 45.0, 57.8, 116.1, 137.2, 215.8.

EXAMPLES 7 AND 8

General Procedure for Methylation (Conversion of Compound 5a to Compound 6a, or of Compound 5b to Compound 6b): Sodium amide (3.64 mmol, assay 90%) was placed in a round bottom flask that was fitted with a reflux condenser, evacuated, and then purged with nitrogen. Freshly distilled benzene (dried over Na/benzophenone) was cannulated into the apparatus, and the mixture was warmed with a heating mantle. The ketone Compound 5a or 5b (1.2 mmol) was then injected, and the reaction mixture was refluxed with continual stirring for 5 hours. The reaction was then cooled to 45° C. (via a hot water bath), and iodomethane (2.9 mmol) (freshly distilled and dried over Drierite) was injected as a single portion. An additional portion of iodomethane (1.57 eq.) was injected 2.5 hours later, and the solution was allowed to react at 45° C. for an additional 15 hours. Saturated aqueous NH$_4$Cl was then added to the cooled solution, and the product was extracted with ethyl ether. The organic layer was then washed with water and brine, and dried over Na$_2$SO$_4$. Removal of excess solvent under vacuum provided crude product 6a or 6b, respectively.

As an alternative, toluene may be used as solvent in this synthesis, in lieu of benzene.

3-(1,3-dimethyl-but-3-enyl)-3,6,6-trimethyl-bicyclo[3.1.1]heptan-2-one (Compound 6a): Purified Compound 6a (0.25 g, 78%) was obtained by column chromatography (with a 90:10/Hexane: EtOAc). $^1$H NMR: (250 MHz, CDCl$_3$), δ 0.89–0.87 (s and d overlapping, 6H), 1.31 (s 3H), 1.33 (s 3H), 1.70 (s 3H), 1.80–1.73 (m 2H), 2.13–1.89 (m 3H), 2.30–2.22 (q 1H), 2.49–2.36 (m 1H), 2.60–2.56 (t 1H), 3.12–3.01 (brd, 1H), 4.72–4.67 (d 2H); $^{13}$C NMR (62.5 MHz, CDCl$_3$) δ 14.7, 21.8, 22.3, 25.8, 26.6, 35.2, 38.1, 40.7, 41.7, 43.1, 45.9, 59.5, 111.3, 145.1, 219.2.

3,6,6-trimethyl-3-(1-methyl-but-3-enyl)bicycle[3.1.1]heptan-2-one (Compound 6b): Purified Compound 6b (0.19 g, 73%) was obtained by column chromatography (with a 90:10/Hexane: EtOAc solvent). $^1$H NMR: (250 MHz, CDCl$_3$), δ 0.79 (s 3H), 0.87–0.84 (d 3H), 1.26–1.23 (d 6H), 1.72–1.58 (m 2H), 1.95–1.79 (m 3H), 2.23–2.19 (m 1H), 2.39–2.31 (m 1H), 2.54–2.49 (t 1H), 3.18–3.04 (m 1H), 4.99–4.87 (m 2H), 5.82–5.62 (m 1H); $^{13}$C NMR (62.5 MHz, CDCl$_3$) δ 14.7, 22.6, 25.8, 26.1, 26.5, 35.4, 36.9, 40.4, 41.6, 43.0, 45.9, 59.5, 115.1, 138.7, 219.3.

EXAMPLES 9 AND 10

(1R, 3S, 5R)-3-[(1R)-1-Methyl-3-oxobutyl]-3,6,6-trimethylbicyclo[3.1.1]heptan-2-one (Compound 7). We developed two syntheses for Compound 7, one starting with Compound 6a, and the other starting with Compound 6b.

(a) Starting from Compound 6a: Finely ground KMnO$_4$ (400 mg, 2.5 mmol) and acidic alumina (Brockmann Activity 1, 1.56 g, 15.3 mmol) were mixed in water (0.4 g, 22 mmol) for five minutes to obtain a homogeneous mixture. The terminal olefin Compound 6a (120 mg, 0.512 mmol) was dissolved in DCM (20 mL) in a round bottom flask. The moistened permanganate/alumina mixture was added to the flask in small portions over 10 minutes with continual stirring. The mixture was allowed to react at room temperature, and the progress of reaction was monitored by TLC (with a 90:10/Hexane: EtOAc solvent). After essentially all starting material had reacted, the crude mixture was filtered through a fritted glass funnel, and the residue was washed with DCM (2×50 mL). Excess solvent was removed via rotary evaporator to leave a yellow oil, which was further purified by column chromatography (90:10/hexane: EtOAc) to give colorless Compound 7 (0.11 g, 89% yield). $^1$H NMR: (250 MHz, CDCl$_3$), δ 0.85–0.82 (d and s overlapping, 6H), 1.17 (s 3H), 1.24 (s 3H), 1.78–1.72 (m 2H), 1.93–1.85 (2 br s, 1H), 2.09–1.96 (m 1H), 2.09 (s 3H), 2.24–2.12 (m 1H), 2.42–2.27 (m 1H), 2.58–2.47 (m 2H), 3.58–3.52 (m 1H); $^{13}$C NMR (62.5 MHz, CDCl$_3$) δ 16.4, 22.6, 24.8, 25.7, 26.3, 30.4, 35.1, 36.9, 41.6, 42.7, 44.6, 47.3, 59.5, 208.2, 219.9.

(b) Starting from Compound 6b: The terminal olefin Compound 6b (220 mg, 1 mmol), mercuric acetate (320 mg, 1 mmol), and methanol (2 mL) were stirred under nitrogen at room temperature for 15 minutes. The mixture was then cannulated into a reaction flask containing a solution of LiCl (9 mg, 0.21 mmol), PdCl$_2$ (18 mg, 0.1 mmol), and CuCl$_2$ (40 mg, 3 mmol) in methanol (1 mL). The mixture was allowed to react at 55° C. for 1 hour. Aqueous NaHCO$_3$ was then added to the mixture, and the product was extracted with ether. The organic layer was washed with water, washed with brine, dried over MgSO$_4$, filtered, and concentrated via rotary evaporator to provide the crude material. Column chromatography (with a 90:10/Hexane: EtOAc solvent) provided Compound 7 in purified form (0.16 g, 73%). $^1$H NMR: (250 MHz, CDCl$_3$), δ 0.85–0.82 (d and s overlapping, 6H), 1.17 (s 3H), 1.24 (s 3H), 1.78–1.72 (m 2H), 1.93–1.85 (2 br s, 1H), 2.09–1.96 (m 1H), 2.09 (s 3H), 2.24–2.12 (m 1H), 2.42–2.27 (m 1H), 2.58–2.47 (m 2H), 3.58–3.52 (m 1H); $^{13}$C NMR (62.5 MHz, CDCl$_3$) δ 16.4, 22.6, 24.8, 25.7, 26.3, 30.4, 35.1, 36.9, 41.6, 42.7, 44.6, 47.3, 59.5, 208.2, 219.9.

EXAMPLE 11

(4R,4aS,6R)-4,4a,5,6,7,8-hexahydro-4,4a-dimethyl-6-(1-chloro-1-methylethyl)-2(3H)-naphthalenone (Compound 8). A dry 3-neck round bottom flask was fitted with a porous gas frit and two gas flow adapters. Under a steady stream of argon, this flask was charged with a solution of purified Compound 7 in glacial acetic acid (99.6%, Aldrich). Anhydrous, gaseous HCl (lecture bottle, Aldrich) was bubbled through the porous frit at room temperature until the solution was saturated with HCl. After 21 hours stirring at room temperature, the mixture was poured into ice, and was then extracted with dichloromethane. The organic layer was washed with water, washed with brine, dried over MgSO$_4$, filtered, and concentrated via the rotary evaporator to provide the crude material in oil form. Recrystallization from hexane provided nootkatone hydrochloride, Compound 8 as colorless needles. Yield, 74%. $^1$H NMR: (250 MHz, CDCl$_3$), δ 5.75 (s, 1H), 2.53–2.34 (m, 2H), 2.31–2.22 (m, 2H), 2.20–1.91 (m, 4H), 1.59 (d, 6H, CH$_3$, J=4.3 Hz), 1.39–1.25 (m, 2H), 1.10 (s, 3H, CH$_3$), 1.00–0.97 (d, 3H, CH$_3$, J=6.76 Hz); $^{13}$C NMR (62.5 MHz, CDCl$_3$) δ 199.7, 170.1, 124.9, 74.1, 45.8, 42.4, 40.8, 40.5, 39.5, 32.3, 30.9, 30.5, 28.5, 17.3, 15.3.

EXAMPLE 12

Nootkatone (Compound 9). Sodium acetate trihydrate (0.22 g, 1.6 mmol) was added to a single-neck round bottom flask that had been fitted with a reflux condenser. A solution of the chloroenone Compound 8 (0.14 g, 0.54 mmol) in glacial acetic acid (4 mL) was injected into the flask, and the mixture was heated to 100° C. and held at that temperature for 2 hours. The reaction mixture was then cooled to room temperature, poured into cold water, and extracted with chloroform. The organic layer was then washed with successive portions of 2% aqueous KOH, 2 N HCl, NaHCO$_3$, and brine, and then dried over MgSO$_4$. The excess solvent was removed via rotary evaporator to provide nootkatone as a yellow oil (93%). The overall yield from β-pinene to nootkatone was 23% using path b, and 25% using path a, both of which are relatively high overall yields. Because the Oxy-Cope reaction and the methylation both provided the desired enantiomeric product, the enantiomeric purity of the final nootkatone product was little changed from that of the β-pinene starting product. Qualitatively, the fragrance of the synthesized nootkatone was identical to the fragrance of nootkatone derived from other sources. NMR data matched that previously reported for nootkatone: $^1$H NMR: (250 MHz, CDCl$_3$), δ 5.77 (s, 1H), 4.75–4.72 (m, 2H), 2.62–2.43 (m, 1H), 2.41–2.22 (m, 4H), 2.09–1.87 (M, 3H), 1.46–1.38 (m, 1H), 1.12–1.10 (m, 4H), 0.98 (d, 3H).

Additionally, alternative phase transfer agents or metal-chelating agents might be used in lieu of 18-crown-6 in the Oxy-Cope reaction to reduce costs, for example quaternary ammonium compounds (quats), PEG [poly(ethyleneglycol)], or tris[2-(2-methoxyethoxy)ethyl]amine.

EXAMPLE 13

In an alternative embodiment, the Oxy-Cope rearrangement and the methylation are carried out in one step, further improving efficiency. An example follows:

3,6,6-trimethyl-3-(1-methyl-but-3-enyl)-bicyclo[3.3.1]heptan-2-one (Compound 6b): A 50-mL round bottom flask, a reflux condenser, a septum, and a magnetic stir bar are placed in a dry box. Under an Ar atmosphere, oil-free KH (0.058 g, 1.44 mmol) is added to the flask. The apparatus is assembled and then removed from the dry box. Freshly distilled THF (14 mL) is injected, and the apparatus is submerged in a jacketed beaker, surrounded by ice, and placed under a positive pressure of Ar. The homoallylic alcohol Compound 4b (0.25 g, 1.2 mmol) is then injected via the reflux condenser. Then 18-crown-6 (0.32 g, 1.2 mmol) in THF (7 mL) is immediately added via cannulation. The mixture is allowed to react at 0° C. for approximately 5 hours. After the Oxy-Cope rearrangement is essentially complete, flame-dried LiBr (0.172 g, 1.98 mmol) in THF (5 mL) is cannulated into the reaction mixture. After 10 minutes, the reaction mixture is warmed to 40° C. with a water bath, and freshly distilled, dry MeI (0.374 mL, 0.85 g, 6 mmol) is injected via syringe. The reaction mixture is warmed to 45° C., and is maintained at that temperature for 17 hours. Additional portions of MeI (0.18 mL, 3 mmol) are added to the reaction mixture every 2 hours during this period. After 17 hours the resulting solution is quickly partitioned between a saturated aqueous NH$_4$Cl solution and ethyl ether. The combined organic layers are washed with water, washed with brine, dried over Na$_2$SO$_4$, filtered, and concentrated. The crude product is purified via column chromatography (with a 9:1/Hexane: EtOAc solvent) to give pure compound 6b.

EXAMPLE 14

Nootkatone made through this synthesis may also be used as an intermediate in preparing nootkatone derivatives, some of which also have activity in repelling termites and other invertebrate pests. For example, following the methods of K. Stevens et al., "Odour character and threshold values of nootkatone and related compounds," *J. Sci. Fd. Agric.*, vol. 21, pp. 590–593 (1970), nootkatone may be converted into isonootkatone, tetrahydronootkatone, 11,12-dihyydronootkatone, or 1,10-dihydronootkatone. Following the methods of B. Zhu et al., "Structure-activity of valencoid derivatives and their repellence to the Formosan subterranean termite," *J. Chem. Ecol.*, vol. 29, pp. 2695–2701 (2003), nootkatone may be converted into nootkatol.

EXAMPLE 15

Figure 2:
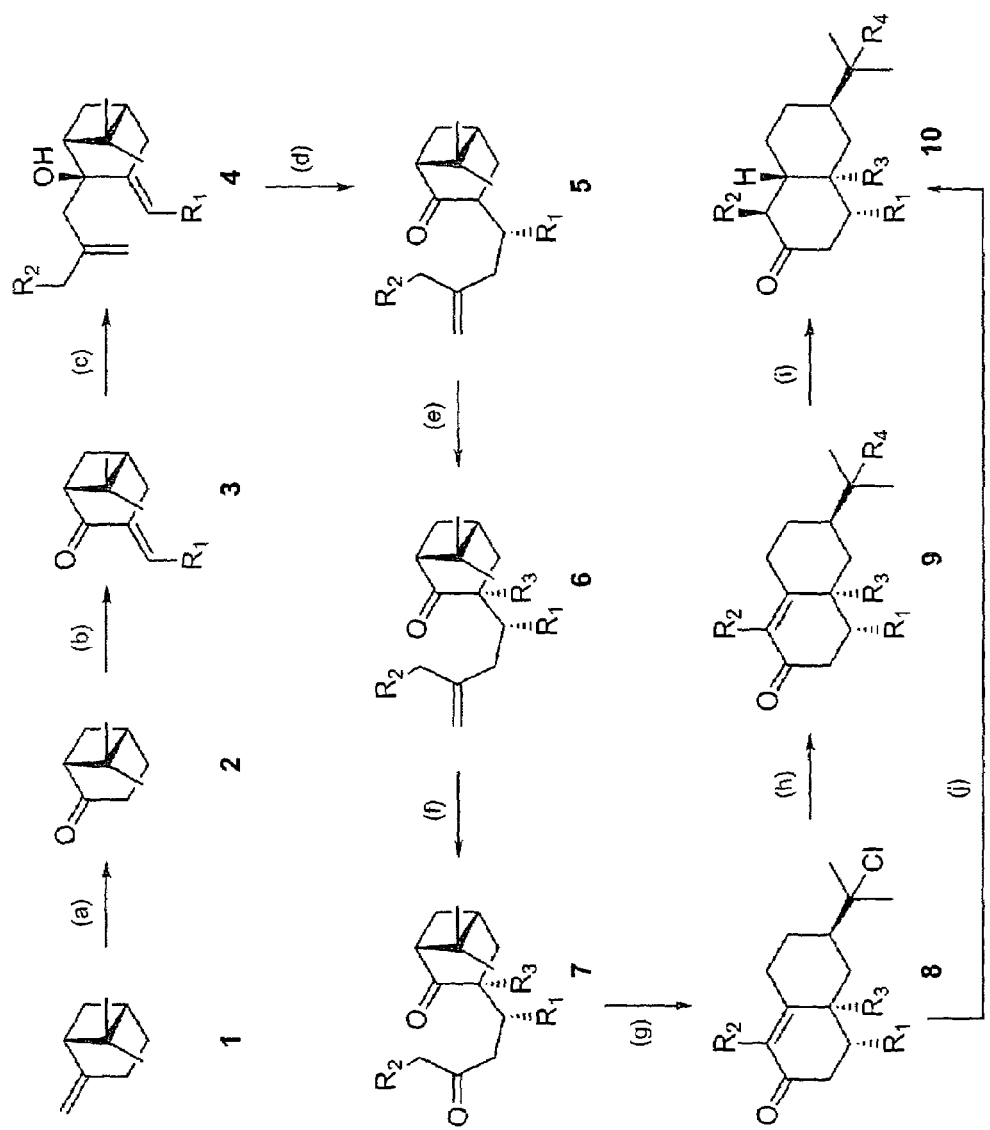
FIG. 2 depicts alternative embodiments of a synthetic scheme in accordance with the present invention.

An alternative synthetic route to substituted nootkatones is depicted in FIG. 2. Except as otherwise stated, the reactions are carried out in the same general manner as previously described for the reaction scheme of FIG. 1. The groups R$_1$ to R$_4$ may be the same or different, e.g., —H or substituted or unsubstituted alkyl groups, for example Et, Pr, i-Pr, Bu, s-Bu, i-Bu, t-Bu,

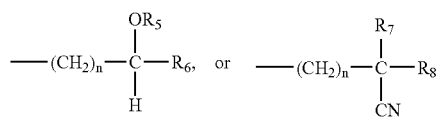

where R$_5$ to R$_8$ may be the same or different, e.g., —H or C$_1$ to C$_4$ substituted or unsubstituted alkyl groups.

The reagents and solvents for the various reaction steps in FIG. 2 are as follows: (a) KMnO$_4$, Al$_2$O$_3$ (b) R$_1$—CHO (c) CH$_2$=C(CH$_2$Cl)(CH$_2$R$_2$), Mg, THF (d) KH, 18-crown-6, THF (e) NaNH$_2$, R$_3$—I, solvent (f) KMnO$_4$, Al$_2$O$_3$ (g) HCl (h) AcOH, NaOAc (i) H$_2$, Pd/C (j) Li (or Na), NH$_3$ (/), EtOH (as in FIG. 3).

EXAMPLE 16

Figure 3:
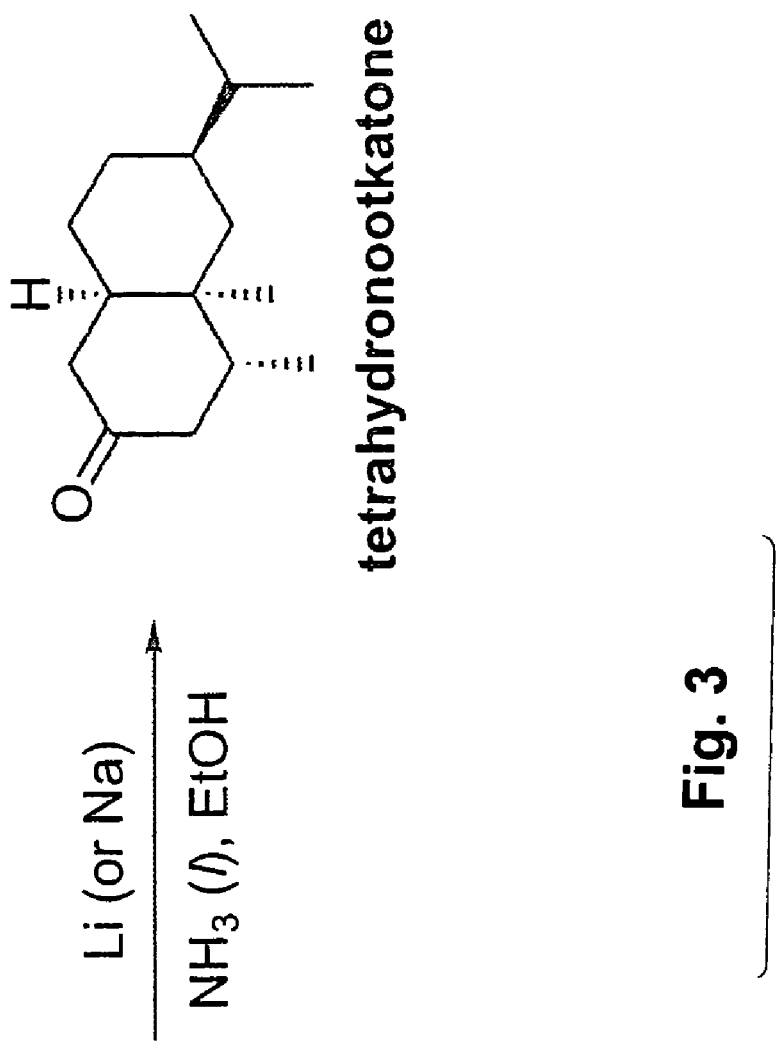
FIG. 3 depicts an alternative synthetic route to tetrahydronootkatone from Compound 8.

An alternative synthetic route to tetrahydronootkatone from Compound 8 is depicted in FIG. 3. The conversion of an enone to the corresponding saturated ketone, as shown in the figure, may be carried out with an alkali metal (e.g., Na or Li) in the presence of a proton source (such as liquid ammonia, ethanol, or both). See generally D. *Caine, Organic Reactions* (New York), vol. 23, pp. 1 ff (1976); and W. Adcock et al., *J. Org. Chem.*, vol. 47, pp. 2951 ff (1982).

The complete disclosures of all references cited in this specification are hereby incorporated by reference. In the event of an otherwise irreconcilable conflict, however, the present specification shall control.

What is claimed is:
1. A process comprising reacting

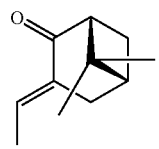

with

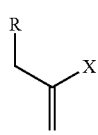

and a metal to produce

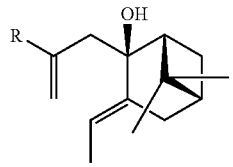

wherein X is a halogen atom; and wherein R is a hydrogen atom or methyl.

2. A process as recited in claim 1; wherein the metal is Mg; and X is Cl.

3. A process as recited in claim 1, additionally comprising the step of subjecting

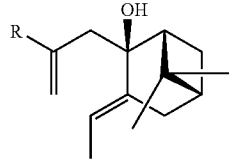

to Oxy-Cope rearrangement to produce

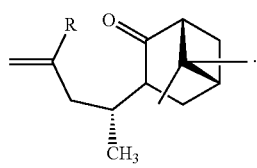

4. A process as recited in claim 3; wherein the metal is Mg; and X is Cl.

5. A process as recited in claim 3; wherein said Oxy-Cope rearrangement is promoted by heating; or by the presence of base and a metal chelating agent; or by the presence of a transition metal catalyst.

6. A process as recited in claim 3; wherein said Oxy-Cope rearrangement is promoted by the presence of potassium hydride and 18-crown-6.

7. A process as recited in claim 3; wherein said Oxy-Cope rearrangement is promoted by the presence of a platinum or palladium catalyst.

8. A process as recited in claim 1, additionally comprising the steps of oxidizing β-pinene to produce nopinone; and reacting the nopinone with acetaldehyde and a base to produce

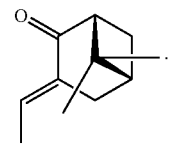

9. A process as recited in claim 3, additionally comprising the steps of reacting

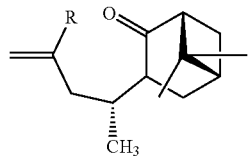

with a methyl halide and a base to produce

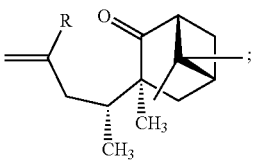

oxidizing the

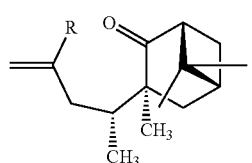

to produce

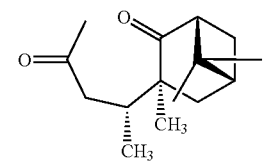

reacting the

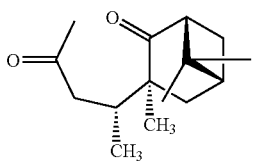

with hydrochloric acid to produce

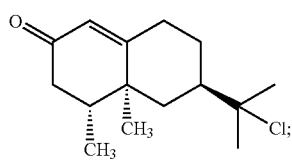

and dehydrohalogenating the

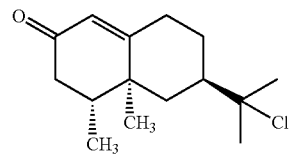

to produce nootkatone.

10. A process as recited in claim 9, additionally comprising the steps of oxidizing β-pinene to produce nopinone; and reacting the nopinone with acetaldehyde and a base to produce

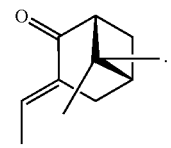

11. A process as recited in claim 10, wherein the metal is Mg; and X is Cl.

12. A process comprising reacting

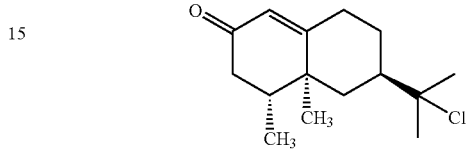

with an alkali metal in the presence of a proton source, whereby tetrahydronootkatone is produced.

13. A process as recited in claim 12, wherein the alkali metal comprises sodium or lithium, and wherein the proton source comprises liquid ammonia.

* * * * *